United States Patent [19]

Malone et al.

[11] Patent Number: 4,710,474

[45] Date of Patent: Dec. 1, 1987

[54] METHOD OF ANALYZING HIGH MOLECULAR WEIGHT DISPERSANTS IN MOTOR OILS

[75] Inventors: Gilbert R. Malone, Perry; Susan K. Skursha, Mentor; Robert M. Jost, Willoughby, all of Ohio

[73] Assignee: The Lubrizol Corporation, Wickliffe, Ohio

[21] Appl. No.: 897,115

[22] Filed: Aug. 15, 1986

[51] Int. Cl.$^4$ ............................................. G01N 33/26
[52] U.S. Cl. ....................................... 436/60; 436/96; 436/106; 436/128; 436/178
[58] Field of Search ...................... 436/60, 61, 96, 106, 436/128, 178

[56] References Cited

U.S. PATENT DOCUMENTS 3,044,860  7/1962  Verley ................................. 436/60
4,234,435 11/1980  Mein Hardt et al. .............. 252/46.6

FOREIGN PATENT DOCUMENTS 223060 12/1983 Japan ..................................... 436/60
1121614 10/1984 U.S.S.R. ................................. 436/60

OTHER PUBLICATIONS

L. Hartman and S. A. Rajendran, The Use of Aqueous Alkalis in the Rapid Determination of Saponification Numbers and Splitting Degree of Oils and Fats, Laboratory Practice, vol. 24, No. 8, pp. 517-518, Aug. 1975
Cox, R., "The Characterization and Quantitative Analysis of Dialkyl and Diaryl Dithiophosphates by Thin-Layer Chromatography and Densitometry," Journal of Chromatography, 105 (1975), pp. 57-64.
Hill, M., et al, "Dialysis of Petroleum Products," presented before the Division of Petroleum Chemistry in American Chemical Society, New York, 9/11-16/1960.
Fialko, M. M. et al, "Kinetics of Dialysis of Motor Oil Additives," All-Union Scientific-Research Institute for Petroleum Processing (VNII NP), No. 9, pp. 25-26, 9/1982.
Jenkins, G. I. et al, "The Analysis of Lubricants and Additive Concentrates Using Spectroscopy and Physical Methods of Separation," The Institute of Petroleum, vol. 51, No. 93 (Jan. 1985).
Coates, J. P., "The Analysis of Lubricating Oils and Oil Additives by Thin-Layer Chromatography," Journal of the Institute of Petroleum, vol. 57, No. 556 (July 1971).
Taulli, T. A., "Evaluation of Isomeric Sodium Alkene-Sulfonates via Methylation and Gas Chromatography," Journal of Chromatographic Science, No. 7 (Nov. 1969).

Primary Examiner—David L. Lacey
Attorney, Agent, or Firm—Karl Bozicevic; Denis A. Polyn; William C. Tritt

[57] ABSTRACT

A method which involves the isolation, analysis and characterization of dispersants present in motor oils is disclosed. The method is particularly useful in connection with the characterization of high molecular weight polybutenyl succinimide dispersants present in finished motor oils so as to provide detailed information with respect to the starting material reactants needed to synthesize such dispersants. The method involves breaking down complexation present in the oil followed by the isolation of the dispersant from the oil via dialysis. The isolated dispersant in the form of a dialysis residue is then acidified and passed through an ion exchange chromatographic column to adsorb acid materials away from the dispersant. Dispersant content and total carbonyl content can then be determined. The dispersant is then subjected to saponification with sodium hydroxide to provide a hydrocarbyl sodium succinate and a polyamine. The saponified material is subjected to further dialysis to separate it from remaining oil and then further acidified. The acidification results in the formation of a corresponding succinic acid and a dialkyl ester derivative. Procedures such as GPC and VPO determinations can then be carried out. Model reactant components can then be prepared and reacted to determine if the reaction product obtained matches the original dispersant being analyzed.

23 Claims, 1 Drawing Figure

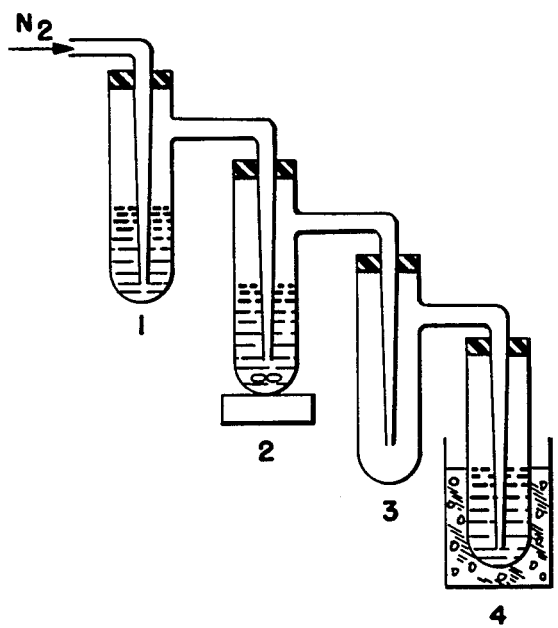

METHOD OF ANALYZING HIGH MOLECULAR WEIGHT DISPERSANTS IN MOTOR OILS

BACKGROUND OF THE INVENTION

Substantial efforts have been made on behalf of the petroleum industry in order to analyze petroleum products at various stages of product production. For example, analysis attempts have been made on crude mineral oil being extracted from the ground or crude vegetable oils extracted from plant life as well as various components present within final motor oils and functional fluids. Such analyses were carried out in order to acquire specific information with respect to the components present witin the petroleum products. Such information allows the manufacturer to: (1) monitor the synthesis and determine the composition and structure of new additives present within petroleum products; (2) obtain additional information with respect to processing and blending control parameters; (3) detect and determine the additive content of lubricants of unknown formulation; and (4) accurately track additive depletion within motor oils and functional fluids during use. These four applications can relate, like the present invention, to uses connected with the analyses of finished products as opposed to an analyses of crude oil materials. The analyses of crude oil materials is distinct from the above in that such analyses is generally directed to obtaining information which will allow refiners to carry out more efficient oil refining techniques.

It is well known that a large number of synthetic chemicals is added to different types of lubricants in order to improve the properties of lubricants during their use within hostile environments such as the high temperature and pressure conditions within an internal combustion engine. Prior to the 1930s, a well-refined mineral oil was sufficient. However, engine demands have increased requiring the use of antioxidants in diesel engine lubricants to prevent oxidation of the base oil with consequent formation of corrosive acids and a rapid increase in viscosity. Subsequently, metal soaps were added as detergents to reduce engine deposits, particularly in the piston ring zone.

The auto industry introduced increasingly powerful internal combustion engines during the 1950s bringing about the development of highly sophisticated motor oils. The Lubrizol Corporation was and continues to be a leader with respect to the development of such sophisticated motor oils which in some instances contain up to 10% of a complex additive mixture conferring properties upon motor oils such as detergency, dispersancy, antioxidant properties, antiwear properties, rust inhibition, viscosity index improvement, pour point depressancy, etc. Different types of engines require different additives with high speed, high compression engines such as present day aviation gas-turbine engines making extreme demands on mineral oils. As the conditions to which the oil is subjected are made increasingly severe, the amount of additive included must be increased in order to provide the properties such as those referred to above. For example, with respect to aviation lubricants, such are now based on diesters or neopentylpolyol esters with hindered phenolic or amine antioxidants and antiwear additives such as aryl phosphates. Present day petroleum chemists consider such lubricant products to consist of 100% additive blends.

With the complexity and amount of additives present within lubricants increasing, it is clear that a determination of the additives present within lubricant oils continually presents analysts with challenging problems. In the past, the elemental analyses for metals such as calcium, barium, zinc and phosphorous might give the analysts useful information. However, at present, there is and has been a distinct trend towards low-ash or ashless dispersants within motor oils making the analyses for such metals of little use. Further, since such metals may be present within a variety of different lubricant additive compounds, and the structure of such compounds containing these metals may vary greatly, analyses for these metals yields little useful information.

In order to deal with such problems such as the increased number of additive compounds being included within lubricants and the increased complexity of the structure of such compounds, analysts have continued to develop sophisticated analytical techniques such as high-performance liquid chromatography (HPLC) and gel permeation chromatography (GPC). (See "Chromatography in Petroleum Analysis," Vol. 11, Knoaus H. Altgelt, Editor, Chevron Research Company, Richmond, Calif., 1979, chapter 17.)

Cox, R., "The Characterization and Quantitative Analysis of Dialkyl and Diaryl Dithiophosphates by Thin-Layer Chromatography and Densitometry," Journal of Chromatography, 105 (1975) pages 57-64. The article discloses methods of identifying dialkyl and diary dithiophosphates (DDPs) by thin-layer chromatography and subsequent quantitative analysis by thin-layer densitometry. The DDPs are reacted with an excess of iodine and the reaction product is chromatographed on silica gel.

Hill, M. et al, "Dialysis of Petroleum Products," presented before the Division of Petroleum Chemistry in American Chemical Society, New York, Sept. 11-16, 1960. The paper discloses some preliminary qualitative and quantitative studies on the application of dialysis for the separation of colloidal components from a variety of petroleum products.

Fialko, M. M. et al, "Kinetics of Dialysis of Motor Oil Additives," All-Union Scientific-Research Institute for Petroleum Processing (VNII NP), No. 9, pages 25-26, September, 1982. The paper discusses the effects of various factors on the process of separation by dialysis as applied to motor oil additives. Specifically, the paper relates to determining information with respect to the kinetics of dialysis on rubber membranes in hydrocarbon solvent medium.

Jenkins, G. I. et al, "The Analysis of Lubricants and Additive Concentrates Using Spectroscopy and Physical Methods of Separation," The Institute of Petroleum, Vol. 51, No. 93 (January 1965). The paper discloses the analysis of lubricants and additive concentrates using spectroscopic techniques in combination with physical methods of separation.

Coates, J. P., "The Analysis of Lubricating Oils and Oil Additives by Thin-Layer Chromatography," Journal of the Institute of Petroleum, Vol. 57, No. 556 (July 1971). The papers discusses the use of thin-layer silica gel chromatography in the routine analysis of lubricating oils and their additives.

Taulli, T. A., "Evaluation of Isomeric Sodium Alkenesulfonates via Methylation and Gas Chromatography," Journal of Chromatographic Science, No. 7 (November 1969). The paper discloses the conversion of non-volatile sodium salts of linear alkene sulfonates in the $C_{16}$ range to volatile compounds which are then qualitatively evaluated by gas chromatography.

Separation methods such as the above referred to chromatography methods have met with some success with respect to the isolation of pure materials. Other isolation methods such as dialysis, classical adsorption chromatography silica and ion exchange resin, thin layer chromatography (TLC) as well as the analytical scale and the quantitative techniques of high performance liquid and gel permeation chromatography have been of use with respect to the routine determination of additives present in lubricants. Such separation techniques are utilized in combination with modern spectrascopic methods such as infrared, nuclear magnetic resonance, ultraviolet, mass spectroscopy and other modifications of these spectroscopic methods in order to identify groups and determine structures of additives present within such isolated components of modern lubricants.

The complexity of isolating and identifying additives within modern lubricants is vastly complicated by the fact that pure chemicals are rarely used as additives in modern lubricant compositions. As opposed to the use of pure chemicals, the additives are often in the form of mixtures of a vast number of different but closely related molecular structures which mixtures can provide improved performance characteristics over a wide range of operation conditions. The method of analysis of the present invention allows for the precise analysis of high molecular weight dispersants within motor oils with consideration to the increase complexity of such dispersants and other components present within motor oils.

SUMMARY OF THE INVENTION

The present invention is a method for analyzing for high molecular weight dispersants in oils of lubricating viscosity such as motor oils. More specifically, the method of analysis involves a number of sophisticated isolation techniques for separating the dispersants present within various compositions away from other additives present and also isolating the dispersants away from the base fluid materials such as the base oil. The method of analysis also involves sophisticated analytical techniques which allow for the characterization of the dispersant itself as well as the reactant components which are utilized in producing such a dispersant.

The method of the present invention is particularly useful in connection with the isolation, analyses and characterization of high molecular weight polybutylsuccinic dispersants present within finished motor oils and more particularly with respect to fully formulated monograde motor oils. The method of the invention provides detailed information with respect to the polyisobutyl substituent or other hydrocarbyl moiety present on the dispersant molecule such as specific information on the carbonyl content and molecular weight distribution of the hydrocarbyl moiety. It is possible for the method to provide information on the polyamine moiety of the dispersant. By making it possible to determine the starting reactant components of the dispersant molecule, the analyst can supply information which makes it possible to recreate the molecule and/or modify the molecule in some manner in order to further increase the performance characteristics of the dispersant molecule.

The dispersant compounds which may be isolated, characterized and analyzed by the present invention include dispersants of the type disclosed in U.S. Pat. No. 4,234,435 which is incorporated herein by reference to disclose dispersants and oils containing such dispersants alone and/or with other additives.

The method of analysis of the present invention involves separating away other additives present within the motor oil which might affect the analysis of the dispersant. More specifically, if a multi-grade oil is being analyzed, the viscosity improvers are precipitated out and the oil is treated with iodine in order to oxidize the zinc dialkyldithiophosphates to their corresponding phosphorothionyl disulfides. Viscosity improvers are not present in mono-grade oils. The treatment with the iodine eliminates the complexation which occurs between the zinc dialkyldithiophosphate and nitrogen dispersants. Accordingly, this simplifies the isolation of the dispersant molecules.

After treating with iodine, the sample is subjected to dialysis in order to remove most of the oil present as well as the phosphorothionyl disulfides formed by adding the iodine. The resulting dialysis residue contains higher molecular weight components including dispersants and detergents.

This dialysis residue is then acidified and passed through an ion exchange chromatographic column in a toluene solution. The acidic materials are adsorbed on the column. The eluate, which includes the dispersant and any remaining oil, passes through the column with the toluene solvent. At this point, determinations of the dispersant content and the total carbonyl content can be carried out by subjecting the eluate to spectrographic and chromatographic analyses.

To carry out further analyses, another portion of the sample of the isolated dispersant obtained via the dialysis is subjected to saponification by adding solid sodium hydroxide and oil. The saponification reaction of the sodium hydroxide with the dispersant yields a hydrocarbyl substituted sodium succinic salt and a polyamine. Since the hydrocarbyl moiety is generally polyisobutyl, the resulting components are generally polyisobutyl sodium succinate and polyamines. At this point, the polyamines are vacuum distilled away. The saponification residue is subjected to dialysis, which is very effective in removing substantially all the oil. The resulting dialysis residue is acidified to its corresponding succinic acid and the dimethylester derivative prepared by the treatment of the acid with diazomethane. Thereafter molecular weight determinations are carried out.

After precise analysis and characterization has taken place with respect to the components of the dispersant molecules, model starting reactant component materials are reacted. The reaction product resulting from these model starting reaction materials are then compared with the originally analyzed dispersant molecules. Various different types of comparisons are possible. For example, the model dispersants could be compared spectrographically, via chromatographic procedures or placed in oils for comparison with the original formulated oil in order to determine if a match exists.

A primary object of the present invention is to provide a method of analyzing the high molecular weight dispersants present within lubricating compositions.

Another object of the invention is to provide a highly specific method of analyzing high molecular weight polybutylsuccinimide dispersant molecules present within motor oils.

An advantage of the present invention is that it allows for the analyst to determine the starting reactant molecules necessary for the formation of the dispersant molecule being analyzed.

A feature of the present invention is that it allows for the analysis of complex dispersant compositions present within motor oils in combination with other additives.

Another advantage of the present invention is that it allows the analyst to carry out an analytical procedure on a motor oil being used in order to determine the amount and rate of depletion of the dispersants within the oil.

Another advantage of the present invention is that it allows the analyst to determine the molecular structure of dispersants present within oils so as to provide information allowing the analyst to speculate how the structure of the dispersant might be modified in order to increase performance.

These and other objects, advantages and features of the present invention will become apparent to those skilled in the art upon reading the present disclosure.

BRIEF DESCRIPTION OF THE DRAWING

The FIGURE is a cross-sectional schematic plan view of the microscale methylation apparatus used to carry out the preparation of dimethylester derivatives of succinic acids.

DETAILED DESCRIPTION OF THE PREFERRED EMBODIMENTS OF THE INVENTION

The present invention which is directed to a detailed method of analyzing high molecular weight dispersants present in lubricating compositions can be divided into 14 distinct steps which will be described below in detail. However, it is to be noted that those skilled in the art upon reading of the present disclosure may, in certain situations, find it advantageous to eliminate, add to, and/or modify these steps to otain some particularly desirable results. Basically the method of the present invention involves the isolation analysis and characterization of dispersant molecules present within lubricating compositions. It might be possible to carry out the various isolation, analysis and characterization steps in different orders and in somewhat different procedural manners in order to obtain similar results. However, the detailed description put forth below has been carried out by the present inventors with a great deal of success with respect to the characterization of dispersant mixtures present within motor oils.

The method of the present invention is particularly useful in connection with the characterization of high molecular weight polybutylsuccinimide dispersants present within finished motor oils. The analytical procedures of the present invention provide detailed information with respect to the starting reactant component materials which must be reacted together in order to synthesize the dispersant molecules present within the motor oils.

Accordingly, the present invention allows not only for the identification of the particular dispersant molecules present within the motor oil but provides specific information with respect to how such dispersant molecules may be synthesized by determining the starting reactant components (the hydrocarbyl substituted succinic acid and polyamine) which were utilized to make such molecules.

The present invention may be used in connection with obtaining information on a range of different types of dispersants. However, the present invention is particularly applicable for analyzing a lubricating composition comprising a major amount of oil of lubricating viscosity and a minor amount of one or more carboxylic derivative compositions produced by reacting at least one substituted succinic acylating agent with a reactant. The reactant is selected from the group consisting of (a) amine characterized by the presence within its structure of at least one nitrogen-containing group, (b) alcohol, (c) reactive metal or reactive metal compounds, and (d) a combination of two or more of any of (a) through (c). The components of (d) are reacted with one or more substituted succinic acylating agents simultaneously or sequentially in any order. The substituted succinic acylating agents consist of substituent groups and succinic groups wherein the substituent groups are derived from polyalkene. The polyalkene is characterized by a Mn value of 1,300 to about 5,000 and a Mw/Mn value of about 1.5 to about 4. The acylating agents are characterized by the presence within their structure of an average of at least 1.3 succinic groups for each equivalent weight of substituent groups.

The 14 individual steps of the present invention are described in detail below. However, an overview of these steps can be seen by referring to Table 1 which is a flow chart of these steps. It should be noted that the present invention is particularly useful in connection with the analysis of dispersants in mono-grade motor oils. However, the invention might be used in connection with multigrade oils which include V.I. (i.e., viscosity improvers). If a V.I. is present, it should be removed at the initial stage. This may be done by dissolving the oil in petroleum ether and adding isopropyl alcohol dropwise while stirring until separation takes place, i.e., the VI will precipitate out.

TABLE 1

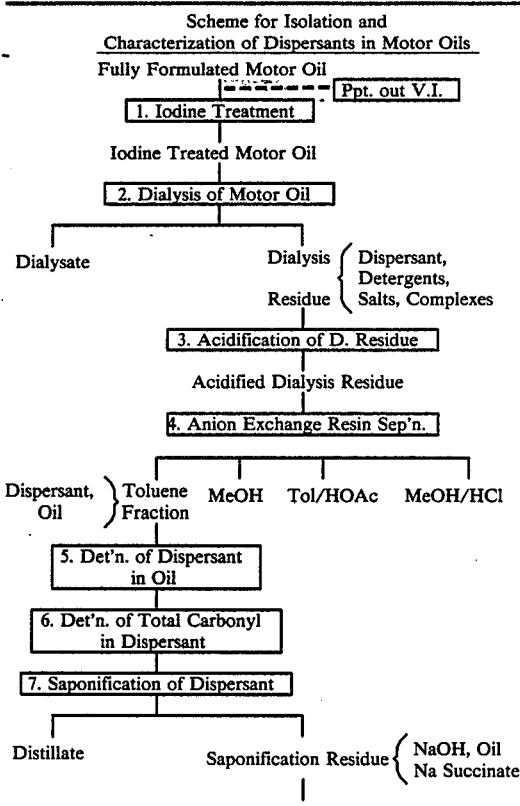

TABLE 1-continued
Scheme for Isolation and Characterization of Dispersants in Motor Oils

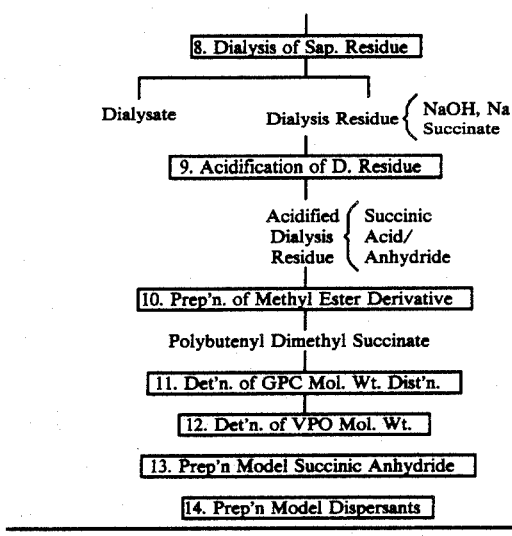

It should be noted that carrying out this method involves the use of hazardous materials, operations and equipment. The information being presented here does not address the safety problems, and the reader is cautioned with respect to carrying out these procedures. The inventors strongly suggest that the reader consults established appropriate safety procedures and health practices and determines the applicability of any regulatory limitations prior to carrying out those procedures. The present inventors point out these cautions with respect to consulting established appropriate safety and health practice procedures and giving consideration with respect to the applicability of regulatory limitations apply with respect to many of the steps described below. However, this caution will not be repeated again. Precaution with respect to some of these procedures may in part be referred to in the A.S.T.M. manual which is incorporated herein by reference.

1. Iodine Treatment

A fully formulated lubricant motor oil is obtained for analysis. Iodine is added to the motor oil in an amount of 20% by weight of excess over the amount of the determined phosphorous concentration in the motor oil. After adding the iodine, the solution is allowed to stand undisturbed until the oxidation is complete. This period is generally about 1 to 2 hours. The sample is then placed on a steam cone and evaporated to dryness.

The iodine treatment is carried out on the fully formulated lubricating oil composition in order to quantitatively oxidize the zinc dialkyldithiophosphates (ZMP) in the oil. The ZMP is oxidized to a phosphorothionyl disulfide ($MP_2$). By utilizing the iodine and oxidizing the ZMP to $MP_2$, it is possible to eliminate complexation which occurs between the ZMP and nitrogen-containing dispersants within the motor oil. Since the nitrogen-containing dispersants are what are to be analyzed, the elimination of such complexation is essential in order to accurately analyze the amount and structure of the dispersants present within the motor oil. Typical ZMP compounds are disclosed in U.S. Pat. No. 3,390,082 which is incorporated herein by reference for purposes of disclosing such compounds and other conventional related oil additives. Some typical examples of related compounds which might be present in a motor oil include the Group II metal salts of phosphorodithioic acids having the structure

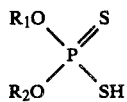

in which $R_1$ and $R_2$ are substantially hydrocarbon radicals. The metals for forming such salts are exemplified by barium, calcium, strontium, zinc, and cadmium. A preferred class of the phosphorodithioates are those having at least about 7.6 carbon atoms in the hydrocarbon radicals per atom of phosphorus in the phosphorodithioate molecular structure. The barium and zinc phosphorodithioates are especially preferred. These substantially hydrocarbon radicals in the phosphorodithioic acid are preferably low or medium molecular weigiht alkyl radicals and alkylphenyl radicals, i.e., those having from about 1 to about 30 carbon atoms in the alkyl group.

2. Dialysis Separation of Fully Formulated Lubricant Oils

After carrying out the iodine treatment, the sample obtained is weighed and placed in a dialysis membrane which is then suspended in a modified Soxhlet extractor. The petroleum ether solvent system is refluxed for 6 hours. After carrying out the reflux procedure, the dialysate fraction diffuses through the membrane and is recovered from the boiling flask. The residue is recovered from inside the membrane.

By carrying out this procedure, the fully formulated lubricating oil compositions can be separated by dialysis into a dialysate and a dialysis residue. The dialysate consists of lower molecular weight components generally having a molecular weight under 1,000 and includes diluent oil and inhibitors. The dialysis residue consists of higher molecular weight components and salts including dispersants and detergents.

3. Acidification of Dialysis Residue

The dialysis residue obtained from step 2 is dissolved in ethyl ether and reacted with 6 normal aqueous hydrochloric acid. The ether extracts are transferred to a tared beaker and evaporated to dryness.

The dialysis residue is acidified with the hydrochloric acid in order to give the acid form of the detergent substrates and the hydrochloride of the basic nitrogens of the dispersant molecule. Accordingly, this step allows the analyst to eliminate complexation with respect to the dispersant molecules so that the component parts can be subjected to further separation and analytical procedures.

4. Anion Exchange Resins Separation of Acidified Dialysis Residue

The acidified dialysis residue is dissolved in a toluene solution and then adsorbed on an anion exchange resin column and eluted into tared beakers using solvent mixtures of increasing polarity and acidity. The solvent is removed.

The anion exchange chromatography utilized during this step separates the dispersants from the detergent substrates generally present in fully formulated motor oils. The polar substrates are physically adsorbed while weak and strong acids are chemically adsorbed. Accordingly, this step allows for the removal of other additives normally present in a fully formulated lubricating oil such as a motor oil.

5. Determination of Dispersant Content by TLC-FID

Samples obtained from step 4 containing polybutenylsuccinimide dispersants are dissolved in petroleum ether. Aliquots are spotted on aluminum coated quartz rods and developed for 18 minutes in a closed chamber using a 3% solution of diethylether in petroleum ether. Following the development, the rods are sequentially scanned with a flame-ionization detector (FID). The output of the FID is amplified and integrated by a 2-pen recorder which produces an analog response (chromatogram) and an integral response. Quantitative results are obtained by measuring the heights of the integral curve for polybutenylsuccinimide dispersant which has been shown to be proportional to the concentration of the dispersant.

6. Determination of Total Carbonyl Content in Succinimide Dispersants by Fourier Transform Infrared Spectroscopy A sample of isolated dispersant in a diluent oil is obtained and an infrared spectrum of the sample is measured in a fixed pathlength KBr infrared cell. The spectrum of the diluent oil is measured in a similar manner, and the reading is subtracted from the sample spectrum to obtain a difference spectrum. The carbonyl absorbances of the difference spectrum are measured, corrected for overlap and used to calculate the imide, amide, and total carbonyl content of the dispersant. Accordingly, this method allows for a determination of the imide/amide distribution and the total carbonyl content in succinimide dispersants by utilizing a Fourier transform IR instrument.

7. Saponification of Isolated Dispersants in Motor Oils

The succinimide dispersant molecules are isolated by procedures as described above. The isolated dispersant is then saponified in oil by the addition of sodium hydroxide. The saponification reaction frees the polyamines from the rest of the molecules, and these polyamines along with a portion of the oil can then be removed from the reaction mixture by a co-distillation procedure under vacuum. The saponification residue consists of sodium succinate, excess sodium hydroxide and the remaining oil. This residue is then subjected to dialysis by the procedure described above in step 2.

This method describes a means of breaking down the succinimide dispersant which has been previously isolated from a finished motor oil. The broken down products can then be further analyzed in order to identify the succinic anhydride and the polyamine which were used in order to synthesize the dispersant.

8. Dialysis of Saponification Residue

In order to remove the oil from the saponification residue, the same procedure described above in step 2 is followed with the following exceptions:

(1) Transfer the entire reaction flask residue into the membrane by rinsing the flask several times with small amounts of petroleum ether and pouring all rinses into the membrane.

(2) Dialysize for 24 hours.

9. Acidification of Dialysis Residue

Acidification of dialysis residue is carried out by obtaining the dialysis residue in accordance with the procedure carried out in step 8 and following the method described in step 3.

10. Preparation of Dimethylester Derivatives of Succinic Acids from Step 9

The acidified material obtained from step 9 is esterified in this step. The sample from step 9 is brought into contact with a diazomethane gas by utilizing a nitrogen purge which carries the diazomethane gas to a solution of carboxylic acids where the methyl ester derivatives of the acids are formed.

This step allows for the preparation of dimethylester derivatives of carboxylic acids formed in step 9 using diazomethane gas.

11. Determination of the GPC Molecular Weight Distribution

Gel permeation chromatography (GPC) is a separation technique for determining molecular weight distribution and average molecular weights of polymers. A solution of a polymer is passed through columns packed with beads of porous crosslinked polystyrene gel. The pores range in average diameter from 200 Å to $10^5$ Å. When a polymer solution is passed through the column, the polymer molecules enter those pores large enough to accept them. Large molecules have only a small number of pores available to enter and will pass through the column rapidly. Small molecules will enter most of the pores and will take longer to pass through the column. The concentration of the species in the solvent stream eluting from the column is monitored continuously by a differential refractometer which measures the difference in refractive index between the pure solvent and polymer solution. This difference is proportional to the concentration of the polymer in solution. The GPC chromatogram is a plot of the concentration versus the elution volume (retention volume). The calibration of the retention volume scale to a molecular weight scale requires a series of standard polymers whose molecular weights have been predetermined by primary methods.

In accordance with the present invention, a number of calibration standards containing known polymers are prepared and chromatographed. The retention time of each standard is measured. The retention times and molecular weight for each standard are plotted to provide a standardization curve. The average molecular weight and molecular weight distribution for sample polymers is then obtained using this curve.

Due to the manner in which gel permeation chromatography operates, the results are particularly useful with respect to obtaining information on a mixture of dispersants present in a finished motor oil. The present inventors have found that the molecular weight of dispersants in motor oil generally varies over a range of about 500 to about 5,000 but may range from 500 to 10,000. Other dispersants have average molecular weights in the range of 1,000 to 6,000 or more particularly 1,300 to 5,000. The present inventors have also found the use of GPC makes it possible to segregate away dispersants having a particular molecular weight range so that specific groups of dispersant molecules can be analyzed separately.

12. Determination of the VPO Molecular Weight Distribution

Vapor phase osmometry (VPO) determines the number average molecular weight, Mn, of a material. For pure organic compounds, the Mn by VPO is the actual molecular weight. The phrase "number average molecular weight" is useful when describing polymers or other materials which do not consist of a single chemical compound. For a material consisting of many molecules of different molecular weights, i.e., a distribution of molecular weights, Mn is the molar average of those molecules, in g/mole. Mathematically, it is the summation of the products of the mole fractions, $f_i$, of those molecules and their corresponding molecular weights, $M_i$:

$$Mn = \Sigma f_i M_i.$$

The principle of VPO is that of vapor pressure depression caused by the presence of a solute in a solution. The amount of depression is proportional to the number of moles of solute per unit weight or volume of solvent.

A drop of sample solution is placed on a metal thermistor in a chamber saturated with solvent vapor. A drop of pure solvent is placed on a nearby, second thermistor. A small temperature difference between the thermistors occurs within minutes due to solvent evaporation from the drop of pure solvent and solvent condensation onto the drop of sample solution. This temperature difference is directly related to vapor pressure depression. A set of different concentrations of a standard with a similar Mn to the unknown is run and a calibration plot is made. Using this plot, the Mn of the sample is calculated. Typically, VPO is used to obtain Mn's of samples in the range of 200 to 3,000 g/mole.

13. Preparation and Analyses of Model Succinic Anhydride

This step of the invention involves the preparation of model starting components which can be reacted in order to form dispersant molecules. The dispersant molecules formed can then be compared with previously analyzed molecules in order to verify the structural determinations.

A model polybutylenesuccinic anhydride molecule can be prepared from polyisobutylene and maleic anhydride. The Mn value of the polyalkene from which the polyisobutylene is derived is at least 1,300 and the product is to contain 1.3 of succinic groups per polyalkene substituent group.

14. Preparation and Analyses of Model Dispersant

A model polybutenyl succinic dispersant can be prepared from the model polybutenyl succinic anhydride of step 13 in combination with tetraethylenepentamine. The polybutenyl succinic dispersant prepared in accordance with this step is the actual molecule which is compared with the dispersant originally being analyzed. The molecule prepared in accordance with this step can be analyzed directly by means such as spectroscopic analysis or it can be blended into an oil with other additives so that its performance can be matched with the performance of the original oil material being analyzed.

EXAMPLES

EXAMPLE PROCEDURE FOR STEP 1

1. Weigh 60 grams of fully formulated oil to the nearest 0.01 g into a 600 ml beaker.
2. Dissolve the sample in 200 ml of petroleum ether using a magnetic stirrer and stir bar.
3. Determine the amount of iodine solution to add using the following equations:
   a. ml $I_2$ solution is equal to (P multiplied by F) divided by I, i.e. $(P \times F) \div I$ where:
   P = (grams of sample taken) (%w P in sample)
   I = grams of $I_2$ weighed to make 100 ml of solution = approx. 0.8
   F = Factor = 4.92
4. Add the $I_2$ solution to the solution of oil.
5. Mix; remove magnetic bar; let stand 1-2 hours with an aluminum foil cover.
6. Add boiling stones and evaporate solvent on the steam bath.

Laboratory Facilities for Step 1

1. Fume hood, walk-in, and bench work area, including standard services.
2. Analytical balance, tare, 240 g capacity, 0.1 mg sensitivity.
3. Top loading balance, 0–100 g tare, 1,200 g capacity, 10 mg sensitivity.
4. Steam bath, concentric-ring, in fume hood.
5. Vacuum oven, variable temperature with maximum of 200° C.

Apparatus for Step 1

1. Standard laboratory glassware
2. Magnetic stirrer with small teflon-coated stir bars
3. Boiling stones, silicone carbide
4. Aluminum foil

Reagents for Step 1

1. Solvents, reagent grade, no residue upon evaporation
   Petroleum Ether (Ligroine)
2. Chemicals, reagent grade
   Iodine, crystalline
3. Iodine solution (should be prepared weekly)
   Weigh 0.8 g iodine to the nearest 0.01 g into a 100 ml volumetric flask. Dissolve the iodine in petroleum ether, warm gently on a steam cone, if necessary, and dilute to volume with petroleum ether.

EXAMPLE PROCEDURE FOR STEP 2

1. Rinse dialysis membrane in petroleum ether and allow to air dry. Place dialysis membrane into 100 ml teflon-lined graduate.
2. Weigh 60 grams of iodine-treated oil blend into the membrane and then record weight to 0.01 g.
3. Attach the membrane to a membrane holder, securing it with a pipe cleaner. Attach the membrane holder to the dialysis "cap" and hang this assembly on the wire handle of the wire screen suspension unit.
4. Insert the suspension unit into the Soxhlet extractor and fill suspension unit with 300 ml petroleum ether. Attach the Soxhlet to the condenser and turn the cooling water on.
5. Add 500 ml of petroleum ether to the one liter flask along with two boiling stones. Grease the flask neck with diluent oil and attach to the base of the Soxhlet.
6. Begin heating by turning on a heating unit equipped with a Variac power switch and adjust power setting to give a gentle reflux.

Dialysate

1. At the end of 6 hours, turn off Variac and allow to cool.
2. Drain the petroleum ether from the Soxhlet extractor into the one-liter flask.
3. Tare a one-liter beaker to which 2 boiling chips have been added.
4. Quantitatively transfer the petroleum ether to the one-liter beaker and place on a steam cone and evaporate until no petroleum ether remains.
5. Place the solvent free dialysate into a vacuum oven and pull a full vacuum (approx. 30 in. Hg) at room temperature for 30 minutes.

6. Remove sample from vacuum. Weigh and record the weight of dialysate.

Dialysis Residue

1. Tare a 250 ml beaker to which 2 boiling stones have been added.
2. Remove the dialysis suspension unit from the Soxhlet and remove the dialysis membrane.
3. Pour the contents of the membrane into a 250 ml tared beaker, rinsing the membrane with solvent, if necessary.
4. Place the dialysis residue solution on a steam cone and evaporate until no petroleum ether remains.
5. Place the solvent-free residue in a vacuum oven at 100° C. for 30 minutes at 30 in. Hg.
6. Remove sample from oven, cool to room temperature, and record the weight of the recovered dialysis residue.

Spectra

1. Obtain infrared spectra on both the dialysate and dialysis residue.

Calculations

Sample weight-SW; Dialysate weight-DW; Residue weight-RW $$\frac{DW}{SW} \times 100 = \% \text{ Dialysate} \quad \frac{RW}{SW} \times 100\% \text{ Dialysis residue}$$

$$\frac{DW + RW}{SW} \times 100 = \% \text{ Recovery}$$

Apparatus for Step 2

1. Standard laboratory glassware
2. Aluminum foil
3. Boiling stones, silicon carbide
4. Top loading balance to 0.01 g accuracy
5. Dialysis unit including:
   a. Latex dialysis membranes, Ramses ®#19 prophylactics, 0.03 in. thickness non-lubricated, plain end
   b. 100 ml graduate with rolled teflon sheet inside
   c. Membrane holder with pipe cleaner fastener
   d. Suspension basket
   e. Soxhlet extractor (approx. 95 mm I.D.) modified to provide a constant fluid level, plus a Variac power controller, heating mantle and a one-liter round bottom flask
   f. Water cooled condenser

Reagents for Step 2

1. Solvent, reagent grade, no residue upon evaporation
   a. Petroleum Ether (Ligroine)

EXAMPLE PROCEDURE FOR STEP 3

1. Dissolve the sample in 100 ml of ethyl ether and transfer the solution to a 250 ml separating funnel.
2. Carefully add 50 ml of 6N HCl to the separatory funnel and shake cautiously, venting frequently.
3. Allow to separate into 2 layers, use a Tesla-type high frequency coil to break up any emulsion and transfer the bottom aqueous layer to another 250 ml separatory funnel.
4. Extract any organic material remaining in the aqueous layer with 100 ml portions of ether until a clear bottom layer is achieved.
5. Combine all ether fractions in a tared 600 ml beaker labeled "RA" containing boiling stones and evaporate the ether on a steam cone.
6. Dry completely in a cool vacuum oven at 30 in. Hg.
7. Obtain infrared spectrum of acidified residue to make sure all inorganic salts have been removed. Repeat procedure, if necessary.

Laboratory Facilities for Step 3

1. Fume hood, walk-in, and bench work area, including standard services
2. Top loading balance, 0–100 g tare, 1,200 g capacity, 10 mg sensitivity
3. Steam bath concentric-ring, in fume hood
4. Vacuum oven, variable temperature with maximum of 200° C.

Apparatus for Step 3

1. Standard laboratory glassware
2. Boiling stones (silicon carbide)
3. High frequency Tesla coil vacuum tester

Reagents for Step 3

1. Solvents, reagent grade, no residue upon evaporation
   a. Diethyl ether
2. Chemicals, reagent grade
   a. Concentrated HCl
   b. Distilled deionized water
3. Solutions
   a. HCl (6N), add one part concentrated hydrochloric acid to 1 part deionized water and mix well.

EXAMPLE PROCEDURE FOR STEP 4

1. Slurry pack the chromatography column one-half its length (15 cm) with the anion exchange resin.
2. Convert the A-26 resin (i.e. a strongly basic anion exchange resin); to the acetate form as follows:
   Amberlyst A-26 is furnished in the chloride form, moistened with water. To convert to the acetate form, wash with the following:
   1. 1,000 ml 4% Aqueous sodium hydroxide
   2. 400 ml Deionized water
   3. 1,000 ml 4% Aqueous sodium acetate
   4. 400 ml Deionized water
   5. 200 ml Methanol
   6. 200 ml Toluene
   at a rate of 1–2 drops per second.
3. Dissolve the acidified dialysis residue in 50 ml of toluene and add to the column.
4. Elute the solution through the column at a rate of 1–2 drops per second into the first of 4 tared beakers containing boiling stones.
5. Elute with listed portions of each of the following eluents to give four fractions.

| Label | Beaker Size | ml Eluent | Eluent |
|---|---|---|---|
| RA1 | 600 | 250 | Toluene |
| RA2 | 400 | 250 | Methanol |
| RA3 | 400 | 250 | 20% Acetic acid in toluene |
| RA4 | 600 | 350 | 20% HCl in methanol/ether (1:1) v |

6. Evaporate the solvent from each fraction on a steam cone; dry in a vacuum oven (approx. 30 in. Hg) at 100° C. for 30 minutes; cool; record weight recovered.

7. Obtain infrared spectra on each of the fractions.

8. Obtain value for % nitrogen on fraction RA1 (toluene) which contains polybutenyl succinimide dispersant.

Calculations for Step 4

1. % Weight of fraction in original sample:

$$\% \text{ of Fraction} = \frac{\text{fraction weight(g)}}{\text{Original sample used(g)}} \times 100$$

2. % Recovery:

$$\% \text{ recovery} = \frac{gRA_1 + gRA_2 + gRA_3 + gRA_4}{\text{Total grams added to column}} \times 100$$

Laboratory Facilities for Step 4

1. Fume hood, walk-in, and bench work area, including standard services.
2. Top loading balance, 0–100 g tare, 1,200 capacity, 10 mg sensitivity.
3. Steam bath concentric-ring, in fume hood.
4. Vacuum oven, variable temperature with maximum of 200° C.

Apparatus for Step 4

1. Standard laboratory glassware
2. Chromatography columns
3. Boiling chips (silicon carbide)
4. Glass wool Reagents for Step 4

1. Solvents, reagent grade—no residue upon evaporation
   a. Toluene
   b. Methanol
   c. Diethyl ether
   d. Deionized water
2. Chemicals, reagent grade
   a. Sodium hydroxide
   b. Sodium acetate
   c. Acetic acid
   d. HCl, conc.
3. Chromatography packing
   a. Anion exchange resin—Amberlyst A-26 obtained in the hydrochloride form
4. Solutions
   a. 4% Aqueous sodium hydroxide
   b. 4% Aqueous sodium acetate
   c. 20% Acetic acid in toluene
   d. 20% HCl in methanol/ether (1:1)v

EXAMPLE PROCEDURE FOR STEP 5

1. Chamber Saturation
The developing chamber is filled with 100 ml of the developing solvent. A sheet of filter paper is placed along one side of the chamber and moistened with the developing solvent to maintain a vapor-saturated atmosphere.
2. Chromarod Conditioning
Chromarods are stored in the developing chamber, immersed in water, when not in use. The rods are activated by removing from the water and blank scanning once just prior to use.
It is advisable to blank-scan rods once between sample applications to ensure that rods are not contaminated with samples from a previous scan.

3. Sample Application and Development
   a. 1.0 ul of sample is applied in 0.2 ul increments with a blunt-tip syringe. A plexiglass spotting guide is used to aid in applying the sample 2 cm from the bottom of the rod. The spotted rods are allowed to air dry several minutes before placing in the developing chamber.

4. Instrument Conditions for Scanning
Hydrogen Pressure: 0.75 kg/cm$^2$
Air Flow: 2 L/min.
Scan Speed: 4
Recorder Chart Speed: 10 cm/min.
Pen Sensitivity: 200 mv
Integrator Sensitivity: 500 mv Quantitation 1. Area % Polybutenyl Succinimide
The heights of the integral curves for each peak are proportional to the peak areas. The area % of polybutenyl succinimide may, therefore, be determined by the calculation:

$$\text{Area \% Polybutenyl succinimide} = \frac{H_x}{H_t} \times 100 \text{ where,}$$

$H_x$ = height of the integral curve for polybutenyl succinimide
$H_t$ = sum of the heights of the integral curves of all components separated Apparatus for Step 5

1. Iatroscan Mark III Chromatographic Analyzer (Model TH-10)
2. Dry-battery ignitor
3. Alumina chromarods (0.9 mm dia. × 152 mm quartz rods coated with a 75 um layer of sintered alumina)
4. Chromarod spotting guide (plexiglass)
5. Syringe (Hamilton, 1 microliter capacity with blunt tip)
6. Developing chamber (glass)
7. Air pump
8. Hydrogen (tank equipped with a two-stage gas regulator)
   DANGER:
   Extremely flammable
   Gas under pressure
9. Two-pen chart recorder (Allen Datagraph, Model 2125M)
10. Calibrated vials or volumetric flasks Reagents and Solutions for Step 5

1. Petroleum ether (analytical reagent)
   DANGER:
   Extremely flammable
   Harmful if inhaled
   Vapors may cause flash fire
2. Ether, anhydrous (Et$_2$O)
   DANGER:
   Highly volatile, explosive
   Extremely flammable
   Harmful if inhaled
3. Developing solvent:

3 ml Et$_2$O
97 ml petroleum ether

Sample Preparation

A 0.50 gram sample of polybutenyl succinimide in oil is weighed into a tared container. The same is diluted to 5.0 ml with petroleum ether to give a 100 ug/ul final concentration for spotting.

EXAMPLE PROCEDURE FOR STEP 6

1. Dissolve dispersant in diluent oil at known concentration (approx. 0.10–0.15 gm/ml).
2. Fill fixed pathlength infrared cell with dispersant solution (typically cell pathlength is 0.0100 cm).
3. Measure infrared spectrum of solution in the cell. Use Nicolet 60SX Fourier transform infrared spectrometer at a resolution of 2 cm$^{-1}$, and collect at least 32 scans. Collect background spectrum of empty sample chamber, and ratio sample spectrum against background spectrum. Convert ratioed spectrum to absorbance.
4. Clean infrared cell and fill with pure diluent oil. Measure spectrum of pure diluent oil, ratio against background, and convert to absorbance. Subtract base oil absorbance spectrum from sample absorbance spectrum to obtain difference spectrum.
5. Draw baseline between absorbance at 1,810 cm$^{-1}$ and 1,510 cm$^{-1}$ in difference spectrum. Measure peak heights minus baseline at 1,705, 1,665 and 1,645 cm$^{-1}$. Correct the absorbance values at 1,665 and 1,645 cm$^{-1}$ for overlap with each other and the 1,705 cm$^{-1}$ band by the following equations.

$A_{1705}$ = peak height minus baseline at 1705 cm$^{-1}$ $A_{1665}$ = peak height minus baseline at 1665 cm$^{-1}$ $A_{1645}$ = peak height minus baseline at 1645 cm$^{-1}$ c = concentration of sample in diluent oil (gm/ml)

b = pathlength of IR liquid cell (cm)

$E_{1705}$ = extinction coefficient of 1705 cm$^{-1}$ band
  = 664 ml mmol$^{-1}$ cm$^{-1}$ $E_{1665}$ = extinction coefficient of 1665 cm$^{-1}$ band
  = 383 ml mmol$^{-1}$ cm$^{-1}$ $E_{1645}$ = extinction coefficient of 1645 cm$^{-1}$ band
  = 158 ml mmol$^{-1}$ cm$^{-1}$ $$\text{Imide} \frac{\text{mmol}}{\text{gm}} = \frac{A_{1705}}{c\, b\, E_{1705}}$$

$A'_{1665} = A_{1665} - (0.0365 \times A_{1705})$ $A'_{1645} = A_{1645} - (0.0174 \times A_{1705})$ $A''_{1645} = A'_{1645} - (0.68 \cdot A'_{1665})/[1-(0.68 \times 0.33)]$ $A''_{1665} = A'_{1665} - (0.33 \cdot A'_{1645})/[1-(0.68 \times 0.33)]$ $$\text{secondary-Amide} \frac{\text{mmol}}{\text{gm}} = \frac{A''_{1665}}{c\, b\, E_{1665}}$$

$$\text{tertiary-Amide} \frac{\text{mmol}}{\text{gm}} = \frac{A''_{1645}}{c\, b\, E_{1645}}$$

EXAMPLE PROCEDURE FOR STEP 7

1. Quantitatively transfer the isolated polybutenyl succinimide (toluene fraction from Step IV) into a tared 250 ml 3 neck round bottom flask, rinsing the beaker several times with small amounts of diluent oil and then heating it to increase the fluidity of the oil mixture. The total amount of oil added should be approximately equal to the amount of toluene fraction.
2. Calculate the amount of NaOH needed as follows:

$$A = B(C \div B)(D \div E)(F \div G)(H \div I)$$

wherein:
A = grams of NaOH
B = grams of toluene fraction
C = grams of nitrogen
D = one equivalent of nitrogen
E = 14 grams of nitrogen
F = 4 equivalents of NaOH
G = 1 equivalent of nitrogen
H = 40 grams of NaOH
I = 1 equivalent of NaOH.

Add this amount of solid NaOH beads to the reaction flask.

3. Equip reaction flask with heating mantle, stirring apparatus, thermometer, and distilling head. Attach tared 15 ml graduated receiver and thermometer to distilling head.
4. Lubricate all joints with diluent oil.
5. Plug heating mantle and variable speed mixer into variac.
6. Place tared vacuum trap in Dewar. Prepare dry ice trap in Dewar by filling approx. ½ full with acetone and slowly adding dry ice. Connect dry ice trap to distilling head with vacuum tubing. Connect vacuum trap to vacuum pump through tubing.
7. Place safety shield in front of reaction flask and close hood door as far as possible.

Saponification

8. Stir reaction flask at a moderate rate (mixture should splash lightly around upper half of flask) while heating up to approx. 230° C. over one hour. Adjust variacs as necessary. Hold temperature between approx. 220°–230° C. for ½ hour while stirring. Turn off heating mantle allowing reaction mixture to cool to room temperature while stirring (mixture may sit overnight).

Distillation

9. Attach heating tape to arm of distillation head and plug tape into variac.
10. Lubricate all joints with diluent oil.
11. If mixture has sat overnight, prepare dry ice trap again (see procedure for step 7, substep 5).
12. While stirring moderately, begin heating mixture slowly and start to apply a vacuum to the system. While applying the vacuum, watch for foaming in reaction flask, releasing vacuum if foaming rises up arm of distillation head. Vacuum applied should measure approx. 0.2–0.5 mm Hg with a McLeod vacuum gauge. Turn on variac for heating tape.
13. Heat mixture under vacuum up to approx. 200° C. over approx. one hour and hold between approx. 190°–200° C. for ½ hour. Heat side arm temperature to approx. 180° C.

14. Turn off heating mantle and heating tape while maintaining stirring and vacuum.

15. As mixture cools below 150° C., slowly begin to release vacuum until system is at atmospheric pressure. Allow to cool to room temperature while stirring.

16. Obtain infrared spectrum of reaction flask residue to make sure no succinimide remains by noting the loss of absorbance at 1710 cm$^{-1}$.

Laboratory Facilities and Apparatus for Step 7

1. Fume hood and bench work area, including standard services
2. Top loading balance, 0–100 g tare, 1200 g capacity, 10 mg sensitivity
3. Round bottom flask, 250 ml, 3 neck
4. Distilling head, Claisen head with West condenser, thermometer joint
5. Distilling receiver, graduated to 15 ml
6. Theromometers; one Celcius with adapter suitable for vacuum work; one Celcius to fit standard taper assemblies
7. Vacuum trap and Dewar flask for dry-ice trap
8. Heating Mantle, to fit 250 ml round bottom flask
9. Heating tape
10. Variable power supplies, 3 (Variacs)
11. Variable speed stirring motor, 0–1750 rpm, equipped with stirring assembly suitable for vacuum applications
12. Vacuum Pump and Vacuum Tubing
13. McLeod Vacuum Gauge
14. Safety Shield Reagents for Step 7

1. NaOH Beads
2. Dil Oil, approx. 150 Neutral
3. Acetone, technical grade
4. Dry Ice

EXAMPLE PROCEDURE FOR STEP 8

To remove the oil from the saponification residue, follow the procedure described in step 2 with the following exceptions:

1. Transfer entire reaction flask residue into the membrane by rinsing the flask several times with small amounts of pet ether and pouring all rinses into the membrane.
2. Dialyze 24 hours, turn off variac and allow to cool.

EXAMPLE PROCEDURE FOR STEP 9

Follow the method described in step 3 to acidify the dialysis residue obtained by following the procedure of step 8.

EXAMPLE PROCEDURE FOR STEP 10

1. Set up apparatus and facilities for step 10 as shown in FIG. 1.
2. Weigh 0.25 g of acidified dialysis residue from Step 9 into a 50 ml beaker.
3. Dissolve sample in approx. 15–20 ml solution of 10% methanol in diethyl ether. Transfer solution to tube 4 and place tube in an ice water bath.
4. Add the following reagents to tube 2 shown in FIG. 1:
   1. 2 ml of 30% aqueous potassium hydroxide
   2. 1 vial (2 ml) of 20% Diazalid
   3. 2 ml absolute methanol
   Agitate the contents of tube 2 of FIG. 1 with magnetic stirring.

5. Quickly connect all tubes and purge a stream of nitrogen through the system.
6. When the yellow color disappears from tube 2 of FIG. 1 and shut off nitrogen and magnetic stirrer.
7. Discard contents of tube 2 from set up of FIG. 1 and replenish as in sub-step 4 above.
8. Repeat sub-steps 5–7 above until all vials containing Diazalid are used.
9. Remove another tube from the apparatus and transfer contents to a 50 ml tared beaker containing a boiling stone. Evaporate solvent from the beaker on a steam cone.
10. Obtain an infrared spectrum of sample to check for complete disappearance of acid and formation of ester. If any acid remains, repeat sub-steps 3–10 above.

Laboratory Facilities and Apparatus for Step 10

1. Fume hood and bench work area, including standard services.
2. Top loading balance, 0–100 g tare, 1200 g capacity, 10 mg sensitivity.
3. Steam bath, concentric ring, in fume hood.
4. Standard laboratory glassware.
5. Magnetic stirrer with small teflon-coated stir bar.
6. Boiling stones, silicon carbide.

Reagents for Step 10

1. Solvents, reagent grade, no residue upon evaporation.
   a. Methyl alcohol, absolute
   b. Diethyl ether
2. Chemicals, reagent grade
   a. Potassium hydroxide
   b. N-methyl-N-nitroso-p-toluenesulfonamide
3. Solutions
   a. 10% methanol in diethyl ether (V/V)
   b. 30% aqueous potassium hydroxide (W/V)
   c. 20% Diazalid—weigh 0.4 g N-methyl-N-nitroso-p-toluenesulfonamide to the nearest 0.01 g into a 4 ml screw vial. Add 2 ml diethyl ether. Shake to dissolve. Prepare 4 vials.
4. FIG. 1 drawing.

FIG. 1 is a cross-sectional schematic plan view of the macroscale methylation apparatus used to carry out step 10. FIG. 1 shows tests tubes 1, 2, 3 and 4 which are each 25×150 mm test tubes with side arms. Each of the test tubes 1–4 is equipped with a rubber stopper and the tubes are interconnected with 7 mm glass tubing tapered at each lower end which extends into the tubes. About 5 ml of diethyl ether is added to test tube 1. To test tube 2 is added about 2 ml of methyl alcohol, 2 ml of 30% KOH and 2 ml of Diazalid (i.e., N-methyl-N-nitroso-p-toluenesulfonamide in diethyl ether). Test tube 4 is packed in ice and to test tube 4 is added carboxylic acid dissolved in 10% methanol in diethyl ether.

EXAMPLE PROCEDURE FOR STEP 11

A sample of material obtained from step 10 can be dissolved in a suitable known solvent and subjected to GPC. The concentration of the material dissolved can then be monitored by a differential refractometer which measures the difference in refractive index between the pure known solvent and the solution being analyzed. The difference is proportional to the concentration of the dispersant in the solution. The GPC chromatogram provides a plot of the dispersant concentration versus the elution volume (retention volume). Specific information about the dispersant in the oil being analyzed can then be deduced based on previously checked samples of known dispersant in known oil formulations.

Further information with respect to chromatographic procedures can be obtained from "Chromatography in Petroleum Analysis" (referred to above in the "Background of the Invention") which is now incorporated herein by reference for purposes of disclosing and describing specific procedures useful in connection with the application of chromatography as applied to the procedures of the present invention. More detailed procedural steps for carrying out this procedure are described below:

This procedure describes an analytical method for determining the molecular weight distribution of polymers. Calibration standards whose molecular weights have been predetermined by primary methods are chromatographed. The retention times versus molecular weights for each standard are plotted to provide a standardization curve. The average molecular weight and molecular weight distribution for sample polymers are then obtained using this curve.

Procedure For Step 11

1. Obtain 3 polymer standards whose molecular weight data is in the following range as determined by primary methods:

|  | Mn | Mw |
|---|---|---|
| STD 1 | 900 | 1300 |
| STD 2 | 1800 | 3000 |
| STD 3 | 2800 | 7600 |

2. Prepare a 2% solution of each polymer standard in THF. Allow polymers to solvate for about 2 hours. Filter polymer solutions through Millipore 0.5u filters.

3. Filter and degas the mobile phase. Inject 100 ul of each standard into the chromatograph.

4. Measure the retention time of each calibration standard.

5. Obtain the average molecular weight and molecular weight distribution for sample polymers using the calibration curve.

Apparatus and Column Conditions

Instrument: Waters Model GPCI
Detector: Differential Refractive Index
Auto Sampler: WISP 710B
Data System: Spectra Physics (SP 4200) with Labnet 9200 Computer
Column Set: (5)u-Styragel Columns* (300 cm × 7.8 mm)

| One each of | Mw Working Range |
|---|---|
| 1 × 10$^5$ A° | 10,000–1,000,000 |
| 1 × 10$^4$ A° | 10,000–100,000 |
| 1 × 10$^3$ A° | 1,000–20,000 |
| 2 × 100 A° | 0–1,000 |

Solvent tetrahydrofuran (THF) with 250 ppm BHT (stabilizer)
*Fully porous, highly cross-linked styrene divinylbenzene copolymer particle size: approx. 10 microns

EXAMPLE PROCEDURE FOR STEP 12

Vapor phase osmometry (VPO) is carried out on a sample containing the material obtained from step 10. For example, a sample of material from step 10 can be dissolved in a suitable known solvent and subjected to VPO. A drop of sample solution can be placed on a metal thermistor in a chamber saturated with solvent vapor. A drop of pure solvent can then be placed on a second thermistor. A small temperature differential will occur between the thermistors in a few minutes. This temperature differential is directly related to vapor pressure depression. This VPO procedure is generally used to obtain the average molecular weight (Mn) of a sample having an Mn in the range of about 200 to about 2,000 g/mole.

For details of the procedure of step 12, the inventors refer to the standardized procedures described in the ASTM and specifically incorporate herein by reference D2503-82 for the purpose of disclosing a VPO procedure which may be adapted for use in connection with the present invention. The term D2503-82 refers to a standard test method procedure which is specifically described within the Annual Book of ASTM Standards, a publication well known to analytical chemists.

ANALYSES CHECK

The steps 1–12 described above all relate to various means for isolating, characterizing, and analyzing dispersants in a lubricating oil. When all or any of such steps are carried out, it is possible to check the validity of the results by formulating model reactants (step 13) and reacting such to obtain model dispersant molecules (step 14). The model dispersant can also be included in oils and formulated in reverse to attempt to match the original oil being analyzed with respect to various performance properties.

EXAMPLE PROCEDURE FOR STEP 13

1. Weigh 1500 g Parapol 1300 and 178 g maleic anhydride into round bottom flask.

2. Equip flask as described below in "Laboratory Facilities and Apparatus for Step 13" describing the round bottom flask.

3. Heat contents of flask to 125° C. Blow 158 g Cl$_2$ into reaction mixture at the rate of 20 g/hr. over the next 8 hours.

4. During chlorination, raise temperature from 125° C. to 190° C.

5. Blow N$_2$ through reaction mixture for 16 hours, keeping the temperature at 190° C.

6. Strip reaction flask for one hour at 210° C. and 7 mm Hg. Record weight of recovered malan.

7. Cool and bottle product.

8. Obtain the following analyses on the product: vis @ 100° C.; % Cl$_2$; % unreacted hydrocarbon; Sap No.; TAN; % free malan 9. Prepare the methyl ester derivative of the succinic anhydride by the method described in step 10.

10. Obtain GPC and VPO molecular weight data on the methyl succinate derivative by the method described in steps 11 and 12.

Laboratory Facilities and Apparatus for Step 13

1. Fume hood and bench work area, including standard services.

2. Round bottom flask, 3 liter 4 necked, equipped with thermocouple, stirrer, subsurface gas inlet tube, heated air condenser, Friedrichs condenser, 2 dry ice traps, air trap, orthotoluidine trap* (1 ml o-toluidien per 50 ml Dist. H$_2$O) and caustic trap.
*Color change in trap indicates that chlorination rate is too fast.

Chemicals for Step 13

1. Exxon Parapol 1300, polyisobutylene (Mn=1,360)
2. Maleic anhydride
3. Cl₂ gas

EXAMPLE PROCEDURE FOR STEP 14

Preparation of Model Dispersant

1. Weight 330 g of the model polybutenyl succinic anhydride prepared previously and 238 g diluent oil into round bottom flask.
2. Equip flask as described above for facilities for step 13 in sub-step 2.
3. Heat contents of flask to 120° C. and start N₂ blowing at 0.1 cubic foot per hour.
4. While raising the temperature from 120° to 160° C. over one hour, add 32 grams tetraethylenepentamine.
5. Hold temperature at 160° C. for five hours.
6. Add 9 grams of DD1600 (i.e. a porous silicone oxide based filter aid material) and filter through 9 grams DD1600 at 160° C. Filtrate is product.
7. Obtain the following analyses on the product: vis @ 100° C.; TBN; %N; % free amine.

Analysis of Model Dispersant

8. Follow steps 5–12 as described above and shown in Table 1 to analyze the model dispersant in the same manner as the isolated dispersant.

Laboratory Facilities and Apparatus for Step 14

1. Fume hood and bench work area, including standard services.
2. Round bottom flask, one liter, four necked, equipped with thermocouple, stirrer, sub surface gas inlet tube, compensating addition funnel, Dean-Stark trap, and Friedricks condenser.

Chemicals for Step 14

1. Model polybutenyl succinic anhydride prepared in step 13 (Parapol 1300 (Mn 1360)/Malan (1:1.3)mol)
2. Tetraethylenepentamine
3. Diluent Oil
4. DD1600

It is understood that the invention has been disclosed and descirbed herein in what is believed to be its most preferred embodiment. However, it is understood that those skilled in the art, upon reading this disclosure, may contemplate variations and modifications thereof which variations and modifications the present inventors consider to be encompassed by the scope of the present invention.

What is claimed is:

1. A method of analyzing a high molecular weight hydrocarbyl succinimide dispersant in an oil of lubricating viscosity with oil additive components including a metal dialkyl dithiophosphate, comprising the steps of:
   treating a sample of the oil with an amount of iodine sufficient to oxidize the metal dialkyl dithiophosphate in the oil to its corresponding phosphorothionyl disulfide;
   subjecting the sample to dialysis in order to remove a substantial portion of the oil and the phosphorothionyl disulfide formed by treating with iodine to obtain a dialysis residue;
   acidifying the dialysis residue and passing the acidified residue dissolved in an eluant through an ion exchange chromatographic column to absorb the acidified residue onto the column and recovering the eluate;
   subjecting a portion of the eluate to spectrographic analysis so as to analyze hydrocarbyl succinimide dispersant in the eluate.

2. The method of claim 1 wherein the dispersant is a mixture of high molecular weight polybutenyl succinimide dispersants having an average molecular weight in the range of about 500 to about 10,000.

3. The method of claim 1 wherein the oil of lubricating viscosity is a fully formulated motor oil.

4. The method of claim 1 wherein the sample of oil is treated with a 20% by weight excess of iodine over the amount sufficient to oxidize the metal dialkyl dithiophosphate and wherein the metal is zinc.

5. The method as claimed in any one of claims 1, 2, 3 or 4, further comprising:
   subjecting a portion of the eluate to saponification to free polyamide from the dispersant and separating the freed polyamine from the remaining saponification residue by distillation; and
   subjecting the saponfication residue to dialysis to obtain a dialysis residue for analysis.

6. The method of claim 1 wherein the dispersant is a mixture of high molecular weight polyisobutenyl succinimide dispersants having an average molecular weight in the range of about 1,000 to about 6,000.

7. The method of claim 6 wherein the sample of oil is treated with a 20% by weight excess of iodine over the amount sufficient to oxidize the metal dialkyl dithiophosphate and wherein the metal is zinc.

8. A method of analyzing a high molecular weight hydrocarbyl succinimide dispersant in a mono-grade motor oil comprising:
   chemically treating the oil to break down complexation of the dispersant with other motor oil components;
   physically isolating the dispersant from the oil;
   subjecting the isolated dispersant to saponification to free polyamine from the dispersant;
   separating away the freed polyamine from the remaining saponification residue;
   separating away any oil to obtain an eluate containing the saponification residue; and
   conducting analysis of the saponification residue so as to analyze hydrocarbyl succinimide dispersant in the eluate.

9. The method of claim 8 wherein the dispersant includes a high molecular weight polyisobutenyl succinimide.

10. The method of claim 8 wherein, the mono-grade motor oil contains a metal dialkyl dithiophosphate and the chemical treating is carried out by treating the oil with an amount of iodine sufficient to oxidize said metal dialkyl dithiophosphate in the oil to its corresponding phosphorothionyl disulfide.

11. The method of claim 8 wherein the physical isolating of the dispersant is carried out by subjecting the chemically treated oil to dialysis.

12. The method of claim 8 wherein the saponification is carried out by adding NaOH to the isolated dispersant.

13. A method of analyzing a high molecular weight hydrocarbyl succinimide dispersant comprising:
   heating the dispersant in the presence of NaOH at a temperature in the range of about 150° C. to about 300° C. until the dispersant has been substantial saponified such that substantially all polyamine of the dispersant is freed;

separating away the freed polyamine to obtain an eluate containing a saponification residue; and subjecting the saponification residue to analysis so as to analyze hydrocarbyl succinimide dispersant in the eluate.

14. The method of claim 13 wherein the dispersant includes polyisobutenyl dispersant having an average molecular weight in the range of from about 500 to about 10,000.

15. The method of claim 13 wherein the heating is in the range of from about 220° C. to about 230° C.

16. The method of claim 13 wherein the NaOH is in the form of solid NaOH beads.

17. A method of analyzing a high molecular weight polybutenyl succinimide dispersant present in fully formulated multi-grade motor oil which includes as oil additive components a metal dialkyl dithiophosphate and a viscosity index improver, comprising the steps of:

combining the oil with petroleum ether and dropwise adding a lower alkyl alcohol in order to precipitate out the viscosity index improver;

treating a sample of the oil which has had the viscosity index improver precipitated out with an amount of iodine sufficient to oxidize the metal dialkyl dithiophosphate in the oil to its corresponding phosphorodithionyl disulfide;

subjecting the sample to dialysis in order to remove a substantial portion of the oil and the phosphorothionyl disulfide formed by treating with iodine to obtain a dialysis residue;

acidifying the dialysis residue and passing acidified residue dissolved in a solvent through an ion exchange chromatographic column to absorb the acidified residue onto the column and recovering an eluate;

subjecting a portion of the eluate to spectrographic analysis so as to analyze hydrocarbyl succinimide dispersant in the eluate.

18. The method as claimed in any one of claims 17, 6 or 7, wherein, after acidifying and recovering the eluate, subjecting a portion of the eluate to saponification to free polyamine from the dispersant and separating the freed polyamine from the remaining saponification residue by distillation; and subjecting the saponification residue to dialysis to obtain a dialysis residue for analysis so as to analyze hydrocarbyl succinimide dispersant in the eluate.

19. The method of claim 18 wherein the dispersant has a Mn value of about 1,300 to about 5,000.

20. A method of analyzing polyisobutenyl succinimide dispersant having an Mn value of about 1,300 to about 5,000 present in a mono-grade motor oil containing oil additive components including a metal dialkyl dithiophosphate, comprising the steps of:

treating a sample of the oil with an amount of iodine sufficient to oxidize the metal dialkyl dithiophosphate in the oil to its corresponding phosphorodithionyl disulfide;

subjecting the sample to dialysis in order to remove a substantial portion of the oil and the phosphorodithionyl disulfide formed by treating with iodine to obtain a dialysis residue;

acidifying the dialysis residue and passing the acidified residue dissolved in an eluant through an ion exchange chromatagraphic column to absorb the acidified residue onto the column and recovering the eluate;

subjecting a first portion of the eluate to spectrographic analysis so as to analyze hydrocarbyl succinimide dispersant in the eluate;

subjecting a second portion of the eluate to saponification to free polyamine from the dispersant and separating the freed polyamine from the remaining saponification residue by distillation;

subjecting the saponification residue to dialysis to obtain a dialysis residue; and subjecting a portion of the dialysis residue to spectrographic so as to analyze hydrocarbyl succinimide dispersant in the dialysis residue.

21. The method as claimed in claim 20 further comprising:

acidifying a portion of the dialysis residue obtained from the saponification residue to obtain an acidifed material;

esterifying the acidified material; and subjecting the esterified material to analysis.

22. The method of claim 21 wherein the esterified material is subjected to gel permeation chromatography.

23. The method of claim 21 wherein the esterified material is subjected to vapor phase osometry.

* * * * *